United States Patent
Barrow et al.

(10) Patent No.: US 7,351,417 B2
(45) Date of Patent: Apr. 1, 2008

(54) SILKY FEEL COSMETIC EMULSION CHASSIS

(75) Inventors: Stephen Roy Barrow, Trumbull, CT (US); Quynh Pham, Murray Hill, NJ (US); Michael Charles Cheney, Trumbull, CT (US); Brian John Dobkowski, Derby, CT (US); Alexander Lips, Edgewater, NJ (US); Prem Chandar, Closter, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 756 days.

(21) Appl. No.: 10/459,070

(22) Filed: Jun. 11, 2003

(65) Prior Publication Data

US 2004/0185070 A1    Sep. 23, 2004

(51) Int. Cl.
*A61K 8/02* (2006.01)
*A61K 31/74* (2006.01)

(52) U.S. Cl. .................. 424/401; 424/78.02; 524/944

(58) Field of Classification Search ................ 424/400, 424/401, 78.02–78.06; 514/944
See application file for complete search history.

(56) References Cited

U.S. PATENT DOCUMENTS

| | | | |
|---|---|---|---|
| 5,849,315 A * | 12/1998 | Rerek et al. ................ | 424/401 |
| 5,997,887 A * | 12/1999 | Ha et al. ................... | 424/401 |
| 6,086,903 A * | 7/2000 | Trinh et al. ................. | 424/401 |
| 6,187,300 B1 * | 2/2001 | Motley et al. ............... | 424/65 |
| 6,294,182 B1 | 9/2001 | Znaiden et al. | |
| 6,322,799 B1 | 11/2001 | Ilardi et al. | |
| 6,342,470 B1 | 1/2002 | Aronson et al. | |
| 6,368,607 B1 * | 4/2002 | Rerek et al. ................ | 424/401 |
| 6,461,623 B2 * | 10/2002 | Koike et al. ................ | 424/401 |
| 6,495,123 B1 | 12/2002 | Faryniarz et al. | |
| 2001/0055574 A1 * | 12/2001 | Franklin et al. ............. | 424/65 |
| 2002/0131946 A1 * | 9/2002 | Pham et al. ............. | 424/70.11 |

FOREIGN PATENT DOCUMENTS

| | | |
|---|---|---|
| EP | 0 950 400 A2 | 4/1999 |
| EP | 1 092 414 A2 | 10/2000 |
| JP | 09087139 A * | 3/1997 |
| JP | 2002284672 A * | 10/2002 |
| WO | WO 0241849 A2 * | 5/2002 |

* cited by examiner

*Primary Examiner*—Sreeni Padmanabhan
*Assistant Examiner*—Kendra D. Carter
(74) *Attorney, Agent, or Firm*—Milton L. Honig

(57) ABSTRACT

A cosmetic composition is provided which includes a high level of glycerin, a copolymer which is preferably a $C_{10}$-$C_{18}$ acrylates crosspolymer, and a crystalline gel structurant comprising a surfactant and co-surfactant, the structurant having an enthalpy ranging from about 2 to about 15 Joule per gram, wherein the composition has a normal force of from about +5 to about +50 grams thereby achieving a silky sensory feel on skin, the glycerin to copolymer being present in a weight ratio ranging from about 350:1 to about 10:1. Advantageously, the composition has a SkiCon Value ranging from about 10 to about 80.

12 Claims, No Drawings

SILKY FEEL COSMETIC EMULSION CHASSIS

BACKGROUND OF THE INVENTION

1. Field of the Invention

The invention concerns a cosmetic emulsion base with silky feel aesthetics.

2. The Related Art

Aesthetics are an important attribute of a cosmetic lotion or cream. Consumers' judgement of such products is significantly determined by the aesthetics of skinfeel.

Similar to different models of an automobile, cosmetic products often use a common chassis as a base formulation. Product line variants such as moisturizing, anti-aging, herbal and sunscreen formulations usually dose the featured variant additive at levels of less than 5% into a concentrated chassis. Manufacture costs are reduced through use of a chassis system.

The difficulty has been to devise a chassis with the appropriate skinfeel aesthetics. Furthermore, it is desirable to include high levels of glycerin for moisturization. This presents a challenge for thickening and emulsifying agents to overcome the negative feel of glycerin.

U.S. Pat. No. 2002/0,131,946 A1 (Pham et al.) discloses non-sticky cosmetic moisturizing compositions based on glycerin and polymeric wetting agents one of which is described as Pemulen® TR2. Other than removing stickiness, there is no disclosure that these compositions impart any particular skinfeel advantage.

There is a need for a cosmetic concentrate chassis which delivers a silky skinfeel which can be formulated with a variety of actives and promotional ingredients. Still another need is to provide a concentrate with exceptional aesthetics and that imparts a high level of moisturization when applied to the body.

SUMMARY OF THE INVENTION

A cosmetic composition is provided which includes:
(i) a moisturizing effective amount of glycerin;
(ii) a sensory effective amount of a copolymer formed from a major portion of a monoolefinically unsaturated carboxylic acid or anhydride monomer of 3 to 6 carbon atoms and a minor portion of a $C_{10}$-$C_{30}$ acrylate or methacrylate ester monomer;
(iii) from about 1 to about 30% of a crystalline gel structurant comprising a surfactant and co-surfactant in an amount and type exhibiting an enthalpy as measured by Differential Scanning Calorimetry ranging from about 2 to about 15 Joule per gram, and wherein the composition has a normal force of from about +5 to about +50 grams thereby achieving a silky sensory feel on skin, the glycerin to copolymer being present in a weight ratio ranging from about 350:1 to about 10:1.

DETAILED DESCRIPTION OF THE INVENTION

Cosmetic compositions of the present invention are provided with a moisturization effective amount of glycerin which also is known as glycerol in the art. Amounts of glycerin may range from about 10% to about 50%, preferably from 12 to 35%, optimally from 15 to 30% by weight of the composition.

Another component of compositions according to the present invention is that of an emulsifying or non-emulsifying copolymer. The copolymer is formed from a carboxylic monomer in an amount from about 50 to 99% by weight and a long chain acrylate ester in an amount from about 1 to 50% by weight. Amounts of the carboxylic monomer and the acrylate ester are based on the combined weight of both components. It should be understood that more than one carboxylic monomer and more than one acrylate ester can be used in the monomer charge.

Copolymers of this invention can be prepared from a monomeric mixture which contains two essential monomeric ingredients, each in certain proportions, one being a monomeric olefinically-unsaturated carboxylic monomer of 3 to 6 carbon atoms and the other being an acrylic ester having a long chain aliphatic group. Optionally, there is included in the monomeric mixture a crosslinking monomer. Amount of the carboxylic monomer is generally in a major proportion whereas the acrylic ester is used in a minor proportion. In a preferred embodiment, amount of the carboxylic monomer is 80 to 99%, but especially 90 to 98% by weight, whereas amount of the co-monomer is from 20 down to 1%, especially 10 down to 2% by weight, based on the weight of the two monomers.

The copolymers of a carboxylic monomer and an acrylic ester having a long chain aliphatic group can have polymerized therein a minor proportion of a lower alkyl ester of acrylic acid, such as ethyl acrylate, in amount of 0-40% by weight, preferably 5-30%, based on the total monomer charge.

The carboxylic monomers useful in the production of the copolymers of this invention are the olefinically-unsaturated carboxylic acids containing at least one activated carbon-to-carbon olefinic double bond, and at least one carboxyl group, that is, an acid containing an olefinic double bond which readily functions in polymerization because of its presence in the monomer molecule either in the alpha-beta position with respect to a carboxyl group or as a part of a terminal methylene grouping. The anhydrides can also be used, especially maleic anhydride.

The preferred carboxylic monomers for use in the copolymer are the monoolefinic acrylic acids having the general structure:

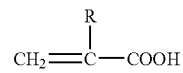

wherein R is a substituent selected from the group consisting of hydrogen, halogen, hydroxyl, lactone, lactam, and the cyanogen (—C—N) groups, monovalent alkyl radicals, monovalent alkaryl radicals and monovalent cycloaliphatic radicals. Of this class, acrylic acid itself is most preferred because of its generally lower cost, ready availability, and ability to form superior polymers. Another particularly preferred carboxylic monomer is maleic anhydride.

The preferred acrylic ester monomers having long chain aliphatic groups are derivatives of acrylic acid having the formula:

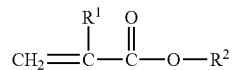

wherein $R^1$ is selected from hydrogen, methyl and ethyl groups and $R^2$ is selected from alkyl groups having from 8 to 30 carbon atoms and oxyalkene and carbonyloxyalkylene groups, preferably alkyl groups of 10 to 22 carbon atoms. The oxyalkene and carbonyloxyalkylene groups are particularly oxyethylene and carbonyloxyethylene groups. Representative higher alkyl acrylic esters are decyl acrylate, lauryl acrylate, stearyl acrylate, behenyl acrylate and myristyl acrylate, and the corresponding methacrylates.

The modified polymers described herein, when tested in the form of 0.2% aqueous mucilages, have viscosity of 100 to 50,000 cps, preferably 250 to 40,000 cps and especially 500 to 35,000 cps. In the form of 1.0%, aqueous mucilages they have viscosity of 1,000 to 100,000 cps, preferably 2,000 to 90,000 cps, and especially 2,500 to 85,000 cps. These viscosities are measured using the Brookfield RVT Model Viscometer at spindle speed of 20 rpm in the pH range of 7.2 to 7.6.

Commercially the emulsifying and non-emulsifying copolymers as described above are available from the Noveon Corporation under the trademarks Pemulen® TR2 and Ultrez® 21. The CTFA name is acrylates/C10-C30 alkyl acrylate crosspolymer. Amounts of the copolymer used within the cosmetic compositions of this invention will range from about 0.01 to about 10%, preferably from about 0.05 to about 1%, more preferably from about 0.1 to about 0.5%, optimally from 0.25 to 0.5% by weight.

Relative amounts by weight of glycerin to the copolymer may range from about 350:1 to about 10:1, preferably from about 150:1 to about 50:1.

A crystalline gel structurant will also be present in compositions according to the present invention. The structurant will include both a surfactant and a co-surfactant. The nature of the surfactant and co-surfactant will depend upon whether the crystalline gel structurant is anionic or nonionic. For structurants that are anionic, the preferred surfactants are $C_{10}$-$C_{22}$ fatty acids and salts (i.e. soap) thereof and particularly combinations of these materials. Typical counterions forming the fatty acid salt are those of ammonium, sodium, potassium, lithium, trialkanolammonium (e.g. triethanolammonium) and combinations thereof. Amounts of the fatty acid to the fatty acid salt when both present may range from about 100:1 to about 1:100, preferably from about 50:1 to about 1:50, and optimally from about 3:1 to about 1:3 by weight. Illustrative fatty acids include behenic acid, stearic acid, isostearic acid, myristic acid, lauric acid, oleic acid, hydroxystearic acid and combinations thereof. Most preferred is stearic acid. Among the fatty acid salts the most preferred is sodium stearate.

The co-surfactant for an anionic crystalline gel structurant typically is a $C_{10}$-$C_{22}$ fatty alcohol, a $C_1$-$C_{200}$ ester of a $C_{10}$-$C_{22}$ fatty acid and particularly combinations of these materials. Relative amounts of the ester to the alcohol when both present may range from about 100:1 to about 1:100, preferably from about 50:1 to about 1:50, and optimally from about 3:1 to about 1:3 by weight. Typical fatty alcohols include behenyl alcohol, stearyl alcohol, cetyl alcohol, myristyl alcohol, lauryl alcohol, oleyl alcohol and combinations thereof. Esters of the fatty acid preferably are polyol esters such as $C_2$-$C_3$ alkoxylated alcohol esters. Among these are the polyethoxy, polypropoxy and block polyethyoxy/polypropoxy alcohol esters. Particularly preferred are such esters as PEG-100 stearate, PEG-20 stearate, PEG-80 laurate, PEG-20 laurate, PEG-100 palmitate, PEG-20 palmitate and combinations thereof.

The relative amount of surfactant and co-surfactant for the anionic structurant may range from about 50:1 to about 1:50, preferably from about 10:1 to about 1:10, and optimally from about 3:1 to about 1:3 by weight.

Nonionic type crystalline gel structurant will have a surfactant and a co-surfactant different than that for the anionic systems. Preferred nonionic structurant surfactants are $C_1$-$C_{200}$ esters of $C_{10}$-$C_{22}$ fatty acid. Esters of the fatty acid preferably are polyol esters such as $C_2$-$C_3$ alkoxylated alcohol esters. Among these are the polyethoxy, polypropoxy and block polyethyoxy/polypropoxy alcohol esters. Particularly preferred are such esters as PEG-100 stearate, PEG-20 stearate, PEG-80 laurate, PEG-20 laurate, PEG-100 palmitate, PEG-20 palmitate and combinations thereof.

The co-surfactant of a nonionic structurant typically may be a combination of a $C_{10}$-$C_{22}$ fatty alcohol, glyceryl esters of a $C_{10}$-$C_{22}$ fatty acid, and a $C_{10}$-$C_{22}$ unesterified fatty acid. Relative amounts of the ester to the alcohol may range from about 100:1 to about 1:100, preferably from about 50:1 to about 1:50, and optimally from about 3:1 to about 1:3 by weight. Relative amounts of the combination of glyceryl ester and fatty alcohol to unesterified fatty acid may range from about 100:1 to about 1:100, preferably from about 50:1 to about 1:50, and optimally from about 3:1 to about 1:3 by weight. Typical fatty alcohols include behenyl alcohol, stearyl alcohol, cetyl alcohol, myristyl alcohol, lauryl alcohol, oleyl alcohol and combinations thereof.

The relative amount of surfactant and co-surfactant in a nonionic structurant may range from about 50:1 to about 1:50, preferably from about 10:1 to about 1:10, and optimally from about 3:1 to about 1:3 by weight.

A crystalline gel structurant is formed by the surfactant and co-surfactant. Indeed, the surfactant and co-surfactant combination in their relative ratio and type of material is defined by an enthalpy which may range from about 2 to about 15, preferably from about 2.5 to about 12, and optimally from about 3.5 to about 8 Joules per gram, as measured by Differential Scanning Calorimetry. Furthermore, the crystalline gel structurant system advantageously may have a melting point ranging from about 30 to about 70° C., preferably from about 45 to about 65° C., and optimally from about 50 to about 60° C.

Compositions of the present invention are not limited by any pH range. However, a preferred pH ranges from about 5.5 to about 8.

Thickeners other than the aforementioned copolymer may but are ordinarily not present in compositions according to this invention. By the term thickener is meant any material which at 2% in water generates a viscosity greater than 5,000 cps, particularly greater than 10,000 cps as measured on a Brookfield RVT model viscometer at spindle speed of 20 rpm in a pH range 7.2 to 7.6.

Normal forces which are positive numbers reflect a silky smooth skinfeel of the formulation. Negative values have been identified with a draggy feel which many consumers dislike. Normal force is measured in the following manner. A rheometer that has a shear rate mode capability and a normal force transducer is utilized to measure the high shear normal force. These devices are available from Rheometric Scientific ARES, TA Instruments AR2000, and Paar Physica MCR. Samples are compressed between concentric parallel plates of diameter 25 mm and gap (vertical distance between the two plates) of 100 microns. The measurements are made in a continuous logarithmic shear sweep mode with a shear rate range of 0.1 to 10,000 $s^{-1}$. Each sweep takes 5 minutes and is conducted at ambient condition (20-25° C.). The normal force is calculated by subtracting the baseline (defined as the normal force value at or near 100 s$^{-1}$) from the highest normal force value measured between 1000 and 10,000 s$^{-1}$. A positive normal force of 5 grams and especially 10 grams or greater is correlated to products/materials with silky sensations during rubbing in application.

The higher the positive value of the normal force the better are the aesthetics. Ordinarily, excellent aesthetics are achieved when the normal force ranges from about +5 to about +50 grams. Particularly desirable is a positive normal force in the range from about +10 to about +60, optimally from about +25 to about +40 grams.

Moisturization is an important aspect along with the sensory feel of compositions of this invention. For this reason, the compositions may advantageously have a Ski-Con Value ranging from about 10 to about 80, preferably from about 20 to about 70, optimally from about 25 to about 60.

The SkiCon Value is measured with a SkiCon 200 instrument. Moisturization is measured on the skin surface through a conductance evaluation (micro Siemens). Depth of measurement is approximately less than 15 μm. The methodology involves use of panelists (usually 10-20 in number). These panelists are requested to pre-wash with a standard Ivory® soap. After 30 minutes, the panelists' skin are measured using the SkiCon 200 instrument. A sample of 0.05 gram experimental product is then applied onto a 5×5 cm area marked on an inner forearm. Post-application measurements are taken two hours after the initial treatment.

Advantageously, compositions of the present invention will have low foamability. Lather Volume as measured by the Lather Volume Test described in U.S. Pat. No. 6,153,208, herein incorporated by reference, ordinarily will be less than 60 ml but preferably less than 30 ml.

A variety of other components may be present in the concentrates of the present invention. Foremost is that of water. Amounts of water may range from about 1 to about 90%, preferably from about 30 to about 80%, optimally from about 50 to about 80% by weight.

Emollient materials may be included in compositions of this invention. These may be in the form of silicone oils, synthetic esters and hydrocarbons. Amounts of the emollients may range anywhere from about 0.1 to about 95 %, preferably between about 1 and about 50% by weight.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about 5×10$^6$ to 0.1 m$^2$/s at 25 C. Among the preferred nonvolatile emollients useful in the present compositions are the polydimethyl siloxanes having viscosities from about 1×10$^{-5}$ to about 4×10$^{-4}$ m$^2$/s at 25 C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.
(4) Wax esters such as beeswax, spermaceti wax and tribehenin wax.
(5) Sterols esters, of which cholesterol fatty acid esters are examples thereof.
(6) Sugar ester of fatty acids such as sucrose polybehenate and sucrose polycottonseedate.

Hydrocarbons which are suitable cosmetically acceptable carriers include petrolatum, mineral oil, $C_{11}$-$C_{13}$ isoparaffins, polyalphaolefins, and especially isohexadecane, available commercially as Permethyl 101A from Presperse Inc.

Humectants of the polyhydric alcohol-type in addition to glycerin can be employed as cosmetically acceptable carriers. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Sunscreen actives may also be included in compositions of the present invention. Particularly preferred are such materials as ethylhexyl p-methoxycinnamate, available as Parsol MCX®, Avobenzene, available as Parsol 1789® and benzophenone-3, also known as Oxybenzone. Inorganic sunscreen actives may be employed such as microfine titanium dioxide, zinc oxide, polyethylene and various other polymers. Amounts of the sunscreen agents when present may generally range from 0.1 to 30%, preferably from 2 to 20%, optimally from 4 to 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.1% to 2% by weight of the composition.

Compositions of the present invention may also contain vitamins. Illustrative water-soluble vitamins are Niacinamide, Vitamin $B_2$, Vitamin $B_6$, Vitamin C and Biotin. Among the useful water-insoluble vitamins are Vitamin A (retinol), Vitamin A Palmitate, Ascorbyl Tetraisopalmitate, Vitamin E (tocopherol), Vitamin E Acetate and DL-panthenol. Total amount of vitamins when present in compositions according to the present invention may range from 0.001 to 10%, preferably from 0.01% to 1%, optimally from 0.1 to 0.5% by weight.

Another adjunct ingredient can be that of an enzyme. Particularly preferred is superoxide dismutase, commercially available as Biocell SOD from the Brooks Company, USA.

Skin lightening agents may be included in the compositions of the invention. Illustrative substances are placental extract, lactic acid, niacinamide, arbutin, kojic acid, resorcinol and derivatives including 4-substituted resorcinols and combinations thereof. Amounts of these agents may range from about 0.1 to about 10%, preferably from about 0.5 to about 2% by weight of the compositions.

Desquamation agents are further optional components. Illustrative are the alpha-hydroxycarboxylic acids and beta-hydroxycarboxylic acids. Among the former are salts of glycolic acid, lactic acid and malic acid. Salicylic acid is representative of the beta-hydroxycarboxylic acids. Amounts of these materials when present may range from about 0.1 to about 15% by weight of the composition.

A variety of herbal extracts may optionally be included in compositions of this invention. Illustrative are green tea, chamomile, licorice and extract combinations thereof. The extracts may either be water soluble or water-insoluble carried in a solvent which respectively is hydrophilic or hydrophobic. Water and ethanol are the preferred extract solvents.

Anti-microbial agents may also be included in the compositions of this invention. Illustrative are trichlosan, trichlocarban, Octopyrox® and zinc pyrithione. Amounts may range from about 0.01 to about 5%, preferably from about 0.1 to about 0.5% by weight of the composition.

Colorants, fragrances, opacifiers and abrasives may also be included in compositions of the present invention. Each of these substances may range from about 0.05 to about 5%, preferably between 0.1 and 3% by weight.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE 1

A series of high level glycerin formulations were evaluated as concentrate chassis to understand their skinfeel properties reflected in their normal force profile. These experiments focused upon the anionic gel structurant surfactant/co-surfactant ratio and effect of Pemulen® TR2. The test formulations are outlined in Table I below.

The surfactant in these formulations is the sodium hydroxide neutralized stearic acid (i.e. sodium stearate). Co-surfactant is the combination of glycerol monostearate/stearamide AMP, glycerol monostearate and cetyl alcohol.

TABLE I

No Pemulen ® TR2 Formulas

| Components | Sample (Weight %) | | | | | | | | |
|---|---|---|---|---|---|---|---|---|---|
| | 1 | 2 | 3 | 4 | 5 | 6 | 7 | 8 | 9 |
| Oil Phase | | | | | | | | | |
| Stearic Acid | 0.485 | 0.965 | 1.455 | 1.940 | 2.540 | 2.908 | 3.394 | 3.878 | 4.363 |
| Glycerol Monostearate/ Stearamide AMP | 2.838 | 2.522 | 2.207 | 1.891 | 1.500 | 1.260 | 0.946 | 0.631 | 0.315 |
| Glycerol Monostearate | 1.325 | 1.177 | 1.030 | 0.883 | 0.700 | 0.588 | 0.441 | 0.294 | 0.147 |
| Cetyl Alcohol | 0.7560 | 0.672 | 0.588 | 0.504 | 0.400 | 0.336 | 0.252 | 0.168 | 0.084 |
| Aqueous Phase | | | | | | | | | |
| Water | 76.332 | 76.272 | 76.210 | 76.148 | 76.070 | 76.028 | 75.963 | 75.901 | 75.839 |
| Disodium EDTA | 0.050 | 0.050 | 0.050 | 0.050 | 0.050 | 0.050 | 0.050 | 0.050 | 0.050 |
| Glycerin | 18.000 | 18.000 | 18.000 | 18.000 | 18.000 | 18.000 | 18.000 | 18.000 | 18.000 |
| Sodium Hydroxide (50% Aqueous Soln.) | 0.124 | 0.248 | 0.370 | 0.494 | 0.650 | 0.740 | 0.864 | 0.988 | 1.112 |
| Glydant Plus ® | 0.090 | 0.090 | 0.090 | 0.090 | 0.090 | 0.090 | 0.090 | 0.090 | 0.090 |

Another set of experiments were conducted to evaluate the system with the presence of 0.3% Pemulen® TR2 and the relationship between surfactant/co-surfactant. The formulas were identical to those in Table I except that 0.3% Pemulen® TR2 was added and 0.3% water removed. The Pemulen® TR2 samples are identified by the letter "P" after the sample number.

The formulations were evaluated for their normal force values at high shear. Tables I, II and III outline the results of that evaluation.

TABLE II

No Pemulen ® TR2

| Sample | Surfactant/Co-Surfactant | Normal Force (gm) |
|---|---|---|
| 1 | 10/90 | −10 |
| 2 | 20/80 | −12 |
| 3 | 30/70 | −17 |
| 4 | 40/60 | −8 |
| 5 | 52/48 | −42 |
| 6 | 60/40 | −18 |
| 7 | 70/30 | −35 |
| 8 | 80/20 | −37 |
| 9 | 90/10 | −93 |

TABLE III 0.3% Pemulen ® TR2

| Sample | Surfactant/Co-Surfactant | Normal Force (gm) |
|---|---|---|
| 1P | 10/90 | +25 |
| 2P | 20/80 | +32 |
| 3P | 30/70 | +33 |
| 4P | 40/60 | +39 |
| 5P | 52/48 | +39 |
| 6P | 60/40 | +37 |
| 7P | 70/30 | +30 |
| 8P | 80/20 | +28 |
| 9P | 90/10 | +10 |

As is evident from Tables II-III, a silky skinfeel as reflected by the positive normal force values is attained only in instances where Pemulen® TR2 is present. Particularly good performance was achieved where the surfactant/co-surfactant ratio ranged from 30:70 to 70:30. Optimum effect was in the 40:60 to 60:40 ratio area.

Sample 5P when formulated without any glycerin and in the presence of 0.3% Pemulen® TR2 exhibited a normal force of 0.0. A control sample similar to sample 5 without either Pemulen® TR2 or glycerin had a normal force of −23. The synergistic combination of optimized crystalline gel structurant network, glycerin, and Pemulen® TR2 yields the highest positive normal forces.

EXAMPLE 2

SkiCon Value readings were taken on formulations according to the present invention utilizing different levels of glycerin. Table IV details the test results. They illustrate the excellent moisturization of high glycerol levels which, except for the presence of crystalline gel structurant and co-polymer, would impart a sticky/tacky sensory feel to the skin. Thus, the presence of Pemulen® and the optimized crystalline gel structurant network despite high glycerin levels provide an unexpected pleasant silky skin sensory while still delivering increased moisturization.

TABLE IV

| % Glycerin | Baseline | SkiCon Reading (2 hours) | SkiCon Value (Change from Baseline) |
|---|---|---|---|
| 10% | 8.58 | 38.42 | 29.83 |
| 18% | 5.97 | 45.39 | 39.42 |
| 26% | 6.94 | 56.72 | 49.78 |
| 35% | 6.44 | 63.61 | 57.17 |

EXAMPLE 3

This Example illustrates the enthalpy values associated with the crystalline gel structurant according to the present invention. The formulas evaluated are nonionic ones listed in Table V below.

TABLE V

| Components | Sample (Weight %) | | |
|---|---|---|---|
| | 1 | 2 | 3 |
| Oil Phase | | | |
| Stearic Acid | 2.075 | 2.371 | 2.669 |
| Glycerol Monostearate/ Stearamide AMP | 1.226 | 1.401 | 1.576 |
| Glycerol Monostearate | 0.572 | 0.654 | 0.735 |
| Cetyl Alcohol | 0.327 | 0.374 | 0.420 |
| PEG-100 Stearate | 1.80 | 1.200 | 0.600 |
| Aqueous Phase | | | |
| Water | 75.860 | 75.860 | 75.860 |
| Disodium EDTA | 0.050 | 0.050 | 0.050 |
| Glycerin | 18.000 | 18.000 | 18.000 |
| Glydant Plus ® | 0.090 | 0.090 | 0.090 |

Enthalpy values for the structurant/co-structurant systems in Table V are listed in Table VI below.

TABLE VI

Nonionic Crystalline Gel Structurant

| Sample | Surfactant:Co-Surfactant | Melting Point (° C.) | Melting/Heating Enthalpy (J/g) |
|---|---|---|---|
| 1 | 30:70 | 52.98 | 7.26 |
| 2 | 20:80 | 51.73 | 6.17 |
| 3 | 10:90 | 51.14 | 10.77 |

EXAMPLE 4

The crystalline gel structurant network of samples 1-8 surfactant/co-surfactant components are reported in Table VII. Enthalpy was measured by Differential Scanning Calorimetry utilizing a heat/cool cycle between 20-80° C. at 5° C./minutes.

TABLE VII

Anionic Crystalline Gel Structurant

| Sample | Surfactant:Co-Surfactant | Melting Point (° C.) | Melting/Heating Enthalpy (J/g) |
|---|---|---|---|
| 1 | 10/90 | — | — |
| 2 | 20/80 | 60.23 | 5.098 |
| 3 | 30/70 | 58.27 | 4.87 |
| 4 | 40/60 | 57.77 | 4.599 |
| 5 | 52/48 | 56.36 | 3.804 |
| 6 | 60/40 | 53.49 | 4.51 |
| 7 | 70/30 | 54.09 | 5.372 |
| 8 | 80/20 | 54.08 | 6.017 |

What is claimed is:

1. A cosmetic composition comprising:
(i) from 10 to 50% by weight of glycerin;
(ii) from 0.01 to 10% by weight of a copolymer formed from a major portion of a monoolefinically unsaturated carboxylic acid or anhydride monomer of 3 to 6 carbon atoms and a minor portion of a $C_{10}$-$C_{30}$ acrylate or methacrylate ester monomer;
(iii) from about 1 to about 30% of a crystalline gel structurant comprising a surfactant and co-surfactant in an amount and type exhibiting an enthalpy as measured by Differential Scanning Calorimetry ranging from about 2 to about 15 Joule per gram, and wherein the composition has a normal force of from about +5 to about +50 grams thereby achieving a silky sensory feel on skin, the glycerin to copolymer being present in a weight ratio ranging from about 350:1 to about 10:1, the crystalline gel structurant being anionic or nonionic;
when anionic the surfactant comprising $C_{10}$-$C_{22}$ fatty acid and a salt of the fatty acid, the fatty acid and salt being present in a ratio from 100:1 to 1:100 and the co-surfactant comprising a $C_{10}$-$C_{22}$ fatty alcohol and a $C_1$-$C_{200}$ ester of a $C_{10}$-$C_{22}$ fatty acid, the alcohol and ester being present in a weight ratio from 100:1 to 1:100; and when nonionic the surfactant comprising a $C_1$-$C_{200}$ polyethoxy or polypropoxy alcohol ester of a $C_{10}$-$C_{22}$ fatty acid and the co-surfactant comprising a mixture of $C_{10}$-$C_{22}$ fatty alcohol, a glyceryl ester of a fatty acid and a $C_{10}$-$C_{22}$ unesterified fatty acid.

2. The composition according to claim 1 wherein the copolymer is an acrylate/$C_{10}$-$C_{30}$ alkyl acrylate crosspolymer.

3. The composition according to claim 1 wherein the fatty acid and salt are present in a weight ratio from about 3:1 to about 1:3.

4. The composition according to claim 1 wherein the alcohol and ester of the anionic co-surfactant are present in a weight ratio from about 3:1 to about 1:3.

5. The composition according to claim 1 wherein the anionic co-surfactant comprises cetyl alcohol and PEG-100 stearate.

6. The composition according to claim 1 wherein the normal force ranges from about +10 to about +60.

7. The composition according to claim 1 wherein glycerin is present from 12 to 35% by weight.

8. The composition according to claim 1 having a SkiCon Value ranging from about 10 to about 80.

9. The composition according to claim 1 wherein the crystalline gel structurant has a melting point ranging from about 30 to about 70° C.

10. The composition according to claim 1 wherein the nonionic surfactant and co-surfactant are present in a weight ratio from about 50:1 to about 1:50.

11. The composition according to claim 1 wherein the glyceryl ester and fatty alcohol of the co-surfactant to the nonionic surfactant are present in a weight ratio of about 100:1 to about 1:100.

12. The composition according to claim 1 wherein a combination of glyceryl ester and fatty alcohol to unesterified fatty acid of the co-surfactant to the nonionic surfactant are present in a weight ratio of about 100:1 to about 1:100.

* * * * *